(12) United States Patent
Jones et al.

(10) Patent No.: US 9,028,469 B2
(45) Date of Patent: May 12, 2015

(54) METHOD OF TREATING CELLULITE

(75) Inventors: Christopher J. Jones, Leicester, MA (US); James C. Hsia, Weston, MA (US); Dilip Y. Paithankar, Natick, MA (US)

(73) Assignee: Candela Corporation, Wayland, MA (US)

( * ) Notice: Subject to any disclaimer, the term of this patent is extended or adjusted under 35 U.S.C. 154(b) by 2307 days.

(21) Appl. No.: 11/529,737

(22) Filed: Sep. 28, 2006

(65) Prior Publication Data

US 2007/0073367 A1    Mar. 29, 2007

Related U.S. Application Data (60) Provisional application No. 60/721,272, filed on Sep. 28, 2005.

(51) Int. Cl.
    *A61N 5/067*  (2006.01)
    *A61N 5/06*   (2006.01)
    *A61B 18/20*  (2006.01)
    *A61B 17/00*  (2006.01)
    (Continued)

(52) U.S. Cl.
    CPC ..... *A61N 5/0616* (2013.01); *A61B 2017/00084* (2013.01); *A61B 2018/00005* (2013.01); *A61B 2018/1807* (2013.01); *A61B 18/203* (2013.01); *A61B 2018/00023* (2013.01); *A61B 2018/00029* (2013.01); *A61B 2018/00452* (2013.01); *A61N 2005/007* (2013.01); *A61N 2005/063* (2013.01); *A61N 2005/0644* (2013.01); *A61N 2005/0659* (2013.01)

(58) Field of Classification Search
    CPC ............ A61B 18/203; A61B 2018/00023; A61B 2018/00005; A61B 2017/00084; A61B 2018/1807; A61B 19/40; A61B 2018/00791
    USPC ....................................... 606/2–19
    See application file for complete search history.

(56) References Cited

U.S. PATENT DOCUMENTS 3,404,350 A   10/1968   Muncheryan
3,538,919 A   11/1970   Meyer et al.
(Continued)

FOREIGN PATENT DOCUMENTS

CA    1041610    10/1978
CA    2131750    1/1996
(Continued)

OTHER PUBLICATIONS

Avram, M., "Cellulite: A Review of its Physiology and Treatment," J. Cosmet. Laser Ther. 6: 181-185 (2004).
(Continued)

*Primary Examiner* — Aaron Roane
(74) *Attorney, Agent, or Firm* — Manelli Selter PLLC; Edward J. Stemberger (57) ABSTRACT

A treatment for subcutaneous fat and/or cellulite includes delivering a beam of radiation to a subcutaneous fat region disposed relative to a dermal interface in a target region of skin. The beam of radiation affects at least one fat cell in the subcutaneous fat region without causing substantial unwanted injury to the epidermal region and causes thermal injury to a dermal region to induce collagen formation to strengthen the target region of skin in a target region of skin. The treatment can include cooling an epidermal region of the target region of skin.

18 Claims, 8 Drawing Sheets

(51) Int. Cl.
  *A61B 18/00* (2006.01)
  *A61B 18/18* (2006.01)
  *A61N 5/00* (2006.01)

(56) References Cited

U.S. PATENT DOCUMENTS

| | | |
|---|---|---|
| 3,693,623 A | 9/1972 | Harte et al. |
| 3,769,963 A | 11/1973 | Goldman et al. |
| 3,834,391 A | 9/1974 | Block |
| 3,900,034 A | 8/1975 | Katz et al. |
| 3,916,143 A | 10/1975 | Farrell |
| 4,388,924 A | 6/1983 | Weissman et al. |
| 4,461,294 A | 7/1984 | Baron |
| 4,608,978 A | 9/1986 | Rohr |
| 4,617,926 A | 10/1986 | Sutton |
| 4,733,660 A | 3/1988 | Itzkan |
| 4,819,669 A | 4/1989 | Politzer |
| 4,854,320 A | 8/1989 | Dew et al. |
| 4,905,690 A | 3/1990 | Ohshiro et al. |
| 4,930,504 A | 6/1990 | Diamantopoulos et al. |
| 4,976,709 A | 12/1990 | Sand |
| 4,985,027 A | 1/1991 | Dressel |
| 5,000,752 A | 3/1991 | Hoskin et al. |
| 5,002,051 A | 3/1991 | Dew et al. |
| 5,019,034 A | 5/1991 | Weaver et al. |
| 5,050,597 A | 9/1991 | Daikuzono |
| 5,057,104 A | 10/1991 | Chess |
| 5,059,192 A | 10/1991 | Zaias |
| 5,102,410 A | 4/1992 | Dressel |
| 5,112,328 A | 5/1992 | Tabaoda et al. |
| 5,133,708 A | 7/1992 | Smith |
| 5,137,530 A | 8/1992 | Sand |
| 5,139,495 A | 8/1992 | Daikuzono |
| 5,140,984 A | 8/1992 | Dew et al. |
| 5,143,063 A | 9/1992 | Fellner |
| 5,151,098 A | 9/1992 | Loertscher |
| 5,165,418 A | 11/1992 | Tankovich |
| 5,182,857 A | 2/1993 | Simon |
| 5,190,032 A | 3/1993 | Zacoi |
| 5,226,907 A | 7/1993 | Tankovich |
| 5,282,797 A | 2/1994 | Chess |
| 5,290,273 A | 3/1994 | Tan |
| 5,304,169 A | 4/1994 | Sand |
| 5,304,170 A | 4/1994 | Green |
| 5,312,395 A | 5/1994 | Tan et al. |
| 5,320,618 A | 6/1994 | Gustafsson |
| 5,334,190 A | 8/1994 | Seiler |
| 5,336,217 A | 8/1994 | Buys et al. |
| 5,344,418 A | 9/1994 | Ghaffari |
| 5,348,551 A | 9/1994 | Spears et al. |
| 5,360,425 A | 11/1994 | Cho |
| 5,374,265 A | 12/1994 | Sand |
| 5,394,492 A | 2/1995 | Hwang |
| 5,397,327 A | 3/1995 | Koop et al. |
| 5,405,368 A | 4/1995 | Eckhouse |
| 5,409,479 A | 4/1995 | Dew et al. |
| 5,423,803 A | 6/1995 | Tankovich et al. |
| 5,425,728 A | 6/1995 | Tankovich |
| 5,437,658 A | 8/1995 | Muller et al. |
| 5,445,146 A | 8/1995 | Bellinger |
| 5,445,634 A | 8/1995 | Keller |
| 5,454,840 A | 10/1995 | Krakovsky et al. |
| 5,464,436 A | 11/1995 | Smith |
| 5,474,549 A | 12/1995 | Ortiz et al. |
| 5,484,432 A | 1/1996 | Sand |
| 5,486,172 A | 1/1996 | Chess |
| 5,522,813 A | 6/1996 | Trelles |
| 5,527,350 A | 6/1996 | Grove et al. |
| 5,569,242 A | 10/1996 | Lax et al. |
| 5,595,568 A | 1/1997 | Anderson et al. |
| 5,606,798 A | 3/1997 | Kelman |
| 5,614,339 A | 3/1997 | Tankovich |
| 5,647,866 A | 7/1997 | Zaias et al. |
| 5,653,706 A | 8/1997 | Zavislan et al. |
| 5,683,380 A | 11/1997 | Eckhouse et al. |
| 5,707,403 A | 1/1998 | Grove et al. |
| 5,713,845 A | 2/1998 | Tankovich |
| 5,735,844 A | 4/1998 | Anderson et al. |
| 5,746,736 A | 5/1998 | Tankovich |
| 5,752,948 A | 5/1998 | Tankovich et al. |
| 5,752,949 A | 5/1998 | Tankovich et al. |
| 5,755,753 A | 5/1998 | Knowlton |
| 5,807,385 A | 9/1998 | Keller |
| 5,810,801 A | 9/1998 | Anderson et al. |
| 5,814,040 A | 9/1998 | Nelson et al. |
| 5,817,089 A | 10/1998 | Tankovich et al. |
| 5,820,626 A | 10/1998 | Baumgardner |
| 5,860,967 A | 1/1999 | Zavislan et al. |
| 5,868,732 A | 2/1999 | Waldman et al. |
| 5,871,480 A | 2/1999 | Tankovich |
| 5,897,549 A | 4/1999 | Tankovich |
| 5,925,035 A | 7/1999 | Tankovich |
| 5,954,710 A | 9/1999 | Paolini et al. |
| 5,964,749 A | 10/1999 | Eckhouse et al. |
| 5,979,454 A | 11/1999 | Anvari et al. |
| 5,997,530 A | 12/1999 | Nelson et al. |
| 6,030,378 A | 2/2000 | Stewart |
| 6,036,684 A | 3/2000 | Tankovich et al. |
| 6,050,990 A | 4/2000 | Tankovich et al. |
| 6,063,074 A | 5/2000 | Tankovich |
| 6,077,294 A | 6/2000 | Cho et al. |
| 6,083,217 A | 7/2000 | Tankovich |
| 6,096,029 A | 8/2000 | O'Donnell, Jr. |
| 6,106,514 A | 8/2000 | O'Donnell, Jr. |
| 6,106,516 A | 8/2000 | Massengill |
| 6,120,497 A | 9/2000 | Anderson et al. |
| 6,120,519 A | 9/2000 | Weber et al. |
| 6,152,917 A | 11/2000 | Tankovich |
| 6,162,211 A | 12/2000 | Tankovich et al. |
| 6,168,590 B1 | 1/2001 | Neev |
| 6,171,301 B1 | 1/2001 | Nelson et al. |
| 6,183,773 B1 | 2/2001 | Anderson |
| 6,206,873 B1 | 3/2001 | Paolini et al. |
| 6,235,016 B1 | 5/2001 | Stewart |
| 6,248,103 B1 | 6/2001 | Tannenbaum et al. |
| 6,267,771 B1 | 7/2001 | Tankovich et al. |
| 6,273,884 B1 | 8/2001 | Altshuler et al. |
| 6,280,438 B1 | 8/2001 | Eckhouse et al. |
| 6,302,863 B1 | 10/2001 | Tankovich |
| 6,315,756 B1 | 11/2001 | Tankovich |
| 6,350,276 B1 | 2/2002 | Knowlton |
| 6,387,089 B1 | 5/2002 | Kreindel et al. |
| 6,405,090 B1 | 6/2002 | Knowlton |
| 6,408,212 B1 | 6/2002 | Neev |
| 6,436,094 B1 | 8/2002 | Reuter |
| 6,511,475 B1 | 1/2003 | Altshuler et al. |
| 6,517,532 B1 | 2/2003 | Altshuler et al. |
| 6,530,920 B1 | 3/2003 | Whitcroft et al. |
| 6,562,054 B1 | 5/2003 | Weber et al. |
| 6,569,156 B1 | 5/2003 | Tankovich et al. |
| 6,600,951 B1 | 7/2003 | Anderson |
| 6,605,079 B2 | 8/2003 | Shanks et al. |
| 6,605,080 B1 | 8/2003 | Altshuler et al. |
| 6,613,040 B2 | 9/2003 | Tankovich et al. |
| 6,613,042 B1 | 9/2003 | Tankovich et al. |
| 6,632,219 B1 | 10/2003 | Baranov et al. |
| 6,648,904 B2 | 11/2003 | Altshuler et al. |
| 6,659,999 B1 | 12/2003 | Anderson et al. |
| 6,663,658 B1 | 12/2003 | Kollias et al. |
| 6,723,090 B2 | 4/2004 | Altshuler et al. |
| 6,733,492 B2 | 5/2004 | Ota et al. |
| 6,743,222 B2 | 6/2004 | Durkin et al. |
| 6,807,297 B1 | 10/2004 | Tankovich et al. |
| 6,920,883 B2 | 7/2005 | Bessette et al. |
| 6,926,683 B1 | 8/2005 | Kochman et al. |
| 6,997,923 B2 | 2/2006 | Anderson et al. |
| 7,020,528 B2 | 3/2006 | Neev |
| 7,060,061 B2 | 6/2006 | Altshuler et al. |
| 7,090,670 B2 | 8/2006 | Sink |
| 7,118,563 B2 | 10/2006 | Weckwerth et al. |
| 7,184,614 B2 | 2/2007 | Slatkine |
| 2002/0161357 A1 | 10/2002 | Anderson et al. |
| 2002/0169442 A1 | 11/2002 | Neev |
| 2002/0173780 A1 | 11/2002 | Altshuler et al. |

(56) References Cited

U.S. PATENT DOCUMENTS

| | | |
|---|---|---|
| 2002/0183789 A1 | 12/2002 | Neev |
| 2003/0032950 A1 | 2/2003 | Altshuler et al. |
| 2003/0036749 A1 | 2/2003 | Durkin et al. |
| 2003/0216719 A1 | 11/2003 | Debenedictis et al. |
| 2004/0005349 A1 | 1/2004 | Neev |
| 2004/0036975 A1 | 2/2004 | Slatkine |
| 2004/0039312 A1 | 2/2004 | Hillstead et al. |
| 2004/0073079 A1 | 4/2004 | Altshuler et al. |
| 2004/0093042 A1 | 5/2004 | Altshuler et al. |
| 2004/0143247 A1 | 7/2004 | Anderson et al. |
| 2004/0162549 A1* | 8/2004 | Altshuler ............ 606/9 |
| 2004/0167499 A1 | 8/2004 | Grove et al. |
| 2004/0167501 A1 | 8/2004 | Island et al. |
| 2004/0167592 A1 | 8/2004 | Grove et al. |
| 2004/0176754 A1 | 9/2004 | Island et al. |
| 2004/0176823 A1 | 9/2004 | Island et al. |
| 2004/0176824 A1 | 9/2004 | Weckwerth et al. |
| 2004/0217675 A1 | 11/2004 | Desilets et al. |
| 2005/0049582 A1 | 3/2005 | DeBenedictis et al. |
| 2005/0055055 A1 | 3/2005 | Neev |
| 2005/0102009 A1 | 5/2005 | Costantino |
| 2005/0131439 A1 | 6/2005 | Brett |
| 2005/0215987 A1 | 9/2005 | Slatkine |
| 2005/0234527 A1 | 10/2005 | Slatkine |
| 2005/0256515 A1 | 11/2005 | Anderson et al. |
| 2006/0004306 A1 | 1/2006 | Altshuler et al. |
| 2006/0004347 A1 | 1/2006 | Altshuler et al. |
| 2006/0009749 A1 | 1/2006 | Weckwerth et al. |
| 2006/0009750 A1 | 1/2006 | Altshuler et al. |
| 2006/0013533 A1 | 1/2006 | Slatkine |
| 2006/0020309 A1 | 1/2006 | Altshuler et al. |
| 2006/0030908 A1 | 2/2006 | Powell et al. |
| 2006/0074468 A1 | 4/2006 | Neev |
| 2006/0129214 A1 | 6/2006 | Da Silva et al. |
| 2006/0142750 A1 | 6/2006 | Da Silva et al. |
| 2006/0224148 A1 | 10/2006 | Cho et al. |
| 2006/0247609 A1 | 11/2006 | Mirkov et al. |
| 2006/0253112 A1 | 11/2006 | Suarez et al. |
| 2006/0259102 A1 | 11/2006 | Slatkine |
| 2006/0265032 A1 | 11/2006 | Hennings et al. |
| 2006/0293722 A1 | 12/2006 | Slatkine et al. |

FOREIGN PATENT DOCUMENTS

| | | |
|---|---|---|
| DE | 195 12 481 | 10/1995 |
| EP | 0 142 671 | 5/1985 |
| EP | 0 292 621 | 11/1988 |
| EP | 0 348 862 | 1/1990 |
| EP | 0 575 274 | 12/1993 |
| EP | 0724866 A1 | 8/1996 |
| EP | 0763371 A2 | 3/1997 |
| GB | 2 123 287 | 2/1984 |
| GB | 2 336 545 | 10/1999 |
| JP | 63-249577 | 10/1988 |
| JP | 64-080309 | 3/1989 |
| JP | 03-193003 | 8/1991 |
| JP | 04-067860 | 3/1992 |
| JP | 04-322668 | 11/1992 |
| JP | 5-329218 | 12/1993 |
| WO | WO 84/02644 | 7/1984 |
| WO | WO 86/02783 | 5/1986 |
| WO | WO 89/00027 | 1/1989 |
| WO | WO 92/16338 | 10/1992 |
| WO | WO 92/19165 | 11/1992 |
| WO | WO 93/05920 | 4/1993 |
| WO | WO 95/15134 | 6/1995 |
| WO | WO 95/15725 | 6/1995 |
| WO | WO 97/37723 | 10/1997 |
| WO | WO 99/27863 | 6/1999 |
| WO | WO 02/35983 | 5/2002 |
| WO | WO 02/053050 | 7/2002 |
| WO | WO 02/087700 | 11/2002 |
| WO | WO 03/005921 | 1/2003 |
| WO | WO 2004/086947 | 10/2004 |
| WO | WO 2005/046793 | 5/2005 |

OTHER PUBLICATIONS

Sadick, et al., "A Prospective Clinical Study to Evaluate the Efficacy and Safety of Cellulite Treatment Using the Combination of Optical and RF Energies for Subcutaneous Tissue Heating," J. Cosmet. Laser Ther. 6: 187-190 (2004).

Alster, T., "Laser Hair Removal: Are the Results Permanent?," Laser Focus: 21-23 (1993).

Anderson et al., "The Optics of Human Skin," The Journal of Investigative Dermatology 77(1): 13-19 (1981).

Anderson et al., "Lasers in Dermatology Provide a Model for Exploring New Applications in Surgical Oncology," International Advances in Surgical Oncology 5: 341-358 (1982).

Anderson et al., "Selective Photothermolysis: Precise Microsurgery by Selective Absorption of Pulsed Radiation," Science 220: 524-527 (1983).

Anderson, R., "Optics of the Skin," in Clinical Photomedicine, ed: Marcel Dekker Inc., New York, New York, 28-31 (1993).

Anderson et al., "Fractional Photothermolysis Redefines Facial Skin Regeneration Science," Aesthetic Buyers Guide Mar./Apr. (2004).

Anvari et al., "Selective Cooling of Biological Tissues During Pulsed Laser Irradiation," Abstract 17, American Society for Laser Medicine and Surgery Abstracts (1995).

Anvari et al., "Dynamic Epidermal Cooling in Conjunction with Laser Treatment of Port-Wine Stains: Theoretical and Preliminary Clinical Evaluations," Lasers in Medical Science 10: 105-112 (1995).

Anvari et al., "A Theoretical Study of the Thermal Response of Skin to Cryogen Spray Cooling and Pulsed Laser Irradiation: Implications for Treatment of Port Wine Stain Birthmarks," Phys. Med. Biol. 40: 1451-1465 (1995).

Anvari et al., "Selective Cooling of Biological Tissues: Application for Thermally Mediated Therapeutic Procedures," Phys. Med. Biol. 40: 241-252 (1995).

Awan, K., "Argon Laser Treatment of Trichiasis," Ophthalmic Surgery 17(10): 658-660 (1986).

Bartley et al., "An Experimental Study to Compare Methods of Eyelash Ablation," Ophthalmology 94: 1286-1289 (1987).

Berlien et al., "Lasers in Pediatric Surgery," Progress in Pediatric Surgery 25: 5-22 (1990).

Campbell, D.C., "Thermoablation Treatment for Trichiasis Using the Argon Laser," Australian and New Zealand Journal of Ophthalmology 18(4): 427-430 (1990).

Dixon et al., "Argon and Neodymium YAG Laser Therapy of Dark Nodular Port Wine Stains in Older Patients," Lasers in Surgery and Medicine 6: 5-11 (1986).

Dover et al., "Pigmented Guinea Pig Skin Irradiated With Q-Switched Ruby Laser Pulses," Arch. Dermatol. 125: 43-49 (1989).

Dover et al., "Illustrated Cutaneous Laser Surgery," in a Practioner's Guide, ed: Appleton & Lange, Norwalk, Connecticut (1990).

Finkel et al., "Pulsed Alexandrite Laser Technology for Noninvasive Hair Removal," Journal of Clinical Laser Medicine & Surgery 15 (5): 225-229 (1997).

Finkelstein et al., "Epilation of Hair-Bearing Urethral Grafts Using the Neodymium: YAG Surgical Laser," The Journal of Urology 146: 840-842 (1991).

Gilchrest et al., "Chilling Port Wine Stains Improves the Response to Argon Laser Therapy," Plastic and Reconstructive Surgery 69(2): 278-283 (1982).

Goldman et al., "Effect of the Laser Beam on the Skin: Preliminary Report," The Journal of Investigative Dermatology 40: 121-122 (1963).

Goldman et al., "Effect of the Laser Beam on the Skin: III. Exposure of Cytological Preparations," The Journal of Investigative Dermatology: 247-251 (1963).

Goldman et al., "Pathology of the Effect of the Laser Beam on the Skin," Nature 197(4870): 912-914 (1963).

Goldman et al., "The Biomedical Aspects of Lasers," JAMA 188(3): 230-234(1964).

(56) References Cited

OTHER PUBLICATIONS

Goldman et al., "Impact of the Laser on Nevi and Melanomas," Archives of Dermatology 90: 71-75(1964).
Goldman et al., "The Effect of Repeated Exposures to Laser Beams," Acta Dermato-Venerologica 44: 264-268 (1964).
Goldman et al., "Radiation From a Q-Switched Ruby Laser," The Journal of Investigative Dermatology: 69-71 (1964).
Goldman et al., "Treatment of Basal Cell Epithelioma by Laser Radiation," JAMA 189(10): 773-775 (1964).
Goldman, L., "Comparison of the Biomedical Effects of the Exposure to Low and High Energy Lasers," Annals of New York Academy of Sciences, 802-831 (1965).
Goldman, L., "Dermatologic Manifestations of Laser Radiation," Proceedings of the First Annual Conference on Biologic Effects of Laser Radiation, Federation of American Societies for Experimental Biology, Supp. No. 14: S-92-S-93 (Jan.-Feb. 1965).
Goldman et al., "Laser Action at the Cellular Level," JAMA 198(6): 641-644 (1966).
Goldman et al., "Investigative Studies With Quartz Rods for High Energy Laser Transmission," Medical Research Engineering: 12-17 (1967).
Goldman et al., "Laser Treatment of Tattoos," JAMA 201(11): 841-844 (1967).
Goldman et al., "Replica Microscopy and Scanning Electron Microscopy of Laser Impacts on the Skin," The Journal of Investigative Dermatology 32(1): 18-24 (1968).
Goldman et al., "Investigative Studies with the Laser in the Treatment from Basal Cell Epitheliomas," Southern Medical Journal 61: 735-742 (1968).
Goldman, L., "The Skin," Arch. Environ. Health 18: 434-436 (1969).
Goldman et al., "Preliminary Investigation of Fat Embolization for Pulsed Ruby Laser Impacts of Bone," Nature 221: 361-363 (1969).
Goldman et al., "Long-Term Laser Exposure of a Senile Freckle," Arch. Environ Health 22: 401-403 (1971).
Goldman et al., "The Laser in Dermatology," Lasers in Medicine, ed: Gordon and Breach, New York, New York: 329-352 (1971).
Goldman, L., "Effects of New Laser Systems on the Skin," Arch. Dermatol. 108: 385-390 (1973).
Goldman, L., "Laser Surgery for Skin Cancer," New York State Journal of Medicine: 1897-1900 (1977).
Goldman, L., "Surgery by Laser for Malignant Melanoma," J. Dermatol. Surg. Oncol. 5(2): 141-144 (1979).
Gossman et al., "Experimental Comparison of Laser and Cryosurgical Cilia Destruction," Ophthalmic Surgery 23(3): 179-182 (1992).
Gossman et al., "Prospective Evaluation of the Argon Laser in the Treatment of Tichiasis," Ophthalmic Surgery 23(3): 183-187 (1992).
Grossman et al., "Damage to Hair Follicles by Normal-Mode Ruby Laser Pulses," Journal of the American Academy of Dermatology 35: 889-894 (1996).
Gustafsson et al., "A Variable Pulsewidth Vascular System for Dermatology," SPIE, 2128: 188-196 (1994).
Haina et al., "Possibilities for the Increase of the Coagulation Depth in Skin with the Argonlaser," in Waidelich W, ed: Springer, Berlin-Heidelberg-New York-Tokyo (1987).
Haina et al., "Improvement of Therapy Results in Treatment of Port Wine Stains with the Argonlaser," in Waidelich W, eds: Springer, Berlin-Heidelberg-New York-Tokyo (1987).
Hellwig et al., "Treatment of Vascular Malformations and Benign Pigmented Lesions by Pulsed Dye Laser, Photoderm VL, and Q-Switched Ruby Laser,"(Abstract) Laryngo-Rhino-Otol. 74: 634-641 (1995).
Huerter et al., "Multiple Eruptive Vellus Hair Cysts Treated with Carbon Dioxide Laser Vaporization," Journ. Dermatol. Surg. Oncol. 13(3): 260-263 (1987).
Iwasaki et al., "Development of Laser Systems for Treatment of Hyperpigmented Skin Lesions," Japanese Journal of Medical Electronics and Biological Engineering 27: 26-34 (1989).
Khan et al., "Optical Clearing of In Vivo Human Skin: Implications for Light-Based Diagnostic Imaging and Therapeutics," Lasers in Surgery and Medicine 34: 83-85 (2004).

Khan et al., "Can Topically Applied Optical Clearing Agents Increase the Epidermal Damage Threshold and Enhance Therapeutic Efficacy?" Lasers in Surgery and Medicine 35: 93-95 (2004).
Kincade, K., "First Laser Hair-Removal System Gains FDA Clearance," Laser Focus World Jun. (1995).
Kincade, K., "New Procedures Push Tissue Studies Beneath the Surface," Laser Focus World August: 57-63 (1995).
Klein et al., "Biological Effects of Laser Radiation I: Threshold Studies and Reversible Depigmentation in Rodent Skin," Nerem Record: 108-109 (1965).
Kuhns et al., "Biological Effects of Laser Radiation II: Effects of Laser Irradiation on the Skin," Nerem Record: (1965).
Kuhns et al., "Laser Injury in Skin," Laboratory Investigation 17(1): 1-13 (1967).
Kuriloff, et al., "Pharyngoesophageal Hair Growth: The Role of Laser Epilation," Case Reports 98(4): 342-345 (1988).
Landthaler et al., "Neodymium-YAG Laser Therapy for Vascular Lesions," Journal of the American Academy of Dermatology 14(1): 107-117 (1986).
Landthaler et al. "Laser Treatment of Port Wine Stains," Dermatologica: Letters to the Editor 175: 156-160 (1987).
Laor et al., "The Pathology of Laser Irradiation of the Skin and Body Wall of the Mouse," Laser Irradiation 47(4): 643-663 (1965).
Lask et al., "Neodymium: Yttrium-Aluminum-Garnet Laser for the Treatment of Cutaneous Lesions," Clinics in Dermatology 13: 81-86 (1995).
Lask et al., "Nonablative Laser Treatment of Facial Rhytides," SPIE 2970: 338-349 (1997).
Maiman, T., "Biomedical Lasers Evolve Toward Clinical Applications," Hospital Management: 39-41 (1966).
Manstein et al., "Fractional Photothermolysis: A New Concept for Cutaneous Remodeling Using Microscopic Patterns of Thermal Injury," Lasers in Surgery and Medicine, 34: 426-438 (2004).
Margolls et al., "Visible Action Spectrum for Melanin-Specific Selective Photothermolysis," Lasers in Surgery and Medicine 9: 389-397 (1989).
Matsumoto, et al., "Ruby Laser Treatment of Melanin Pigmented Skin Lesions Using Toshiba Model LRT-301A Ruby Laser," Journal of Japanese Society for Laser Surgery and Medicine 10(3): 451-454 (1989).
Meloy, T., "The Laser's Bright Magic," National Geographic: 858-881(1966).
Mester et al., "Effect of Laser Beam on the Hair Growth of Mice," Experimental Medicine 19: 628-631 (1967).
Mester et al., "The Stimulating Effect of Low Power Laser-Rays on Biological Systems," Laser Review: 3-6 (1968).
Mester et al., "Effect of Laser Rays on Would Healing," The American Journal of Surgery 122: 532-535 (1971).
Mester et al., "The Biomedical Effects of Laser Application," Lasers in Surgery and Medicine 5: 31-39 (1985).
Milner et al., "Dynamic Cooling for Spatial Confinement of Laser Induced Thermal Damage in Collagen," Abstract 262, American Society for Laser Medicine and Surgery Abstracts (1995).
Miyasaka et al., "Basic and Clinical Studies of Laser for Hyperpigmented Skin Lesions," Journal of the Japanese Society for Laser Surgery and Medicine 11: 117-127 (1991).
Nakaoka et al., "The Square and Uniform Intensity Ruby Laser for the Treatment of Pigmented Skin Lesions," European Journal of Plastic Surgery 15: 23-30 (1992).
Nelson et al., "Dynamic Cooling of the Epidermis During Laser Port Wine Stain Therapy," Abstract 253, American Society for Laser Medicine and Surgery Abstracts (1994).
Nelson et al., "Epidermal Cooling During Pulsed Laser Treatment of Selected Dermatoses," SPIE 2623: 32-39 (1995).
Nelson et al., "Dynamic Epidermal Cooling During Pulsed Laser Treatment of Port-Wine Stain," Arch Dermatol, 131: 695-700 (1995).
Nelson et al., "Dynamic Epidermal Cooling in Conjunction with Laser-Induced Photothermolysis of Port Wine Stain Blood Vessels," Lasers in Surgery and Medicine 19: 224-229 (1996).
Ohshiro et al., "The Ruby and Argon Lasers in the Treatment of Naevi," Annals Academy of Medicine 12(2): (1983).
Ohtsuka et al., "Histological Studies and Clinical Experiences of Ruby Laser Treatment," 107-115 (1991).

(56) References Cited

OTHER PUBLICATIONS

Oshry et al., "Argon Green Laser Photoepilation in the Treatment of Trachomatous Trichiasis," Ophthalmic Plastic and Reconstructive Surgery 10(4): 253-255 (1994).
Parrish et al., "Selective Thermal Effects with Pulsed Irradiation from Lasers: From Organ to Organelle," The Journal of Investigative Dermatology 80(6): 75s-80s (1983).
Polla et al., "Melanosomes are a Primary Target of Q-Switched Ruby Laser Irradiation in Guinea Pig Skin," The Journal of Investigative Dermatology 89(3): 281-286 (1987).
Raulin et al., "Effective Treatment of Hypertrichosis with Pulsed Light: A Report of Two Cases," Ann. Plast. Surg. 39: 169-174 (1997).
Riggle et al., "Laser Effects on Normal and Tumor Tissue," Laser Applications in Medicine and Biology 1: 35-65 (1971).
Rosenfeld et al., "Treatment of Cutaneous and Deep Vascular Lesions with the Nd: YAG Laser," Lasers in Surgery and Medicine 6: 20-23 (1986).
Rosenfeld et al., "The Treatment of Cutaneous Vascular Lesions with the ND: YAG Laser," Annals of Plastic Surgery 21 (3): 223-230 (1988).
Schirmer, K., "Simultaneous Thermal and Optical Breakdown Mode Dual Laser Action," Ophthalmologica 205: 169-177 (1992).
Shapshay et al., "Neodymium-YAG Laser Photocoagulation of Hemangiomas of the Head and Neck," Laryngoscope 97: 323-330 (1987).
Shimbashi et al., "Ruby Laser Treatment of Pigmented Skin Lesions," Aesthetic Plastic Surgery 19: 225-229 (1995).
Smoothbeam Brochure, Candela Corporation, 6 pages (2004).
Solomon et al., "Histopathology of the Laser Treatment of Port-Wine Lesions: Biopsy Studies of Treated Areas Observed up to Three Years After Laser Impacts," The Journal of Investigative Dermatology 50(2): 141-146 (1968).
Stewart, M., "Sebaceous Gland Lipids," Seminars in Dermatology, 11(2): 100-105 (1992).
Svaasand et al., "Melanosomal Heating During Laser Induce Photothermolysis of Port Wine Stains," Abstract 233, American Society for Laser Medicine and Surgery Abstracts (1995).
Svaasand et al., "Epidermal Heating During Laser Induced Photothermolysis of Port Wine Stains: Modeling Melanosomal Heating After Dynamic Cooling the Skin Surface," SPIE 2323: 366-377 (1994).
Takata et al., "Laser-Induced Thermal Damage of Skin," SAM-TR-77-38, USAF School of Aerospace Medicine (1977).
Tanino et al., "Development of Ruby Laser System for Medical Use," (Abstract) Journal of the Japanese Society for Laser Surgery and Medicine 11(4): 93-98 (1991).
Taylor et al., "Treatment of Tattoos by Q-Switched Ruby Laser," Arch. Dermatol. 126: 893-899 (1990).
"Tech News: Lasers and Hair," Circle 21: (1983).
Tsai et al., "Near-infrared Absorption Property of Biological Soft Tissue Constituents," Journal of Medical and Biological Engineering 21(1): 7-14 (2001).
van Gemert et al., "Is There an Optimal Laser Treatment for Port Wine Stains?," Lasers Surg. Med., 6: 76-83 (1986).
van Gemert et al., "Limitations of Carbon Dioxide Lasers for Treatment of Port Wine Stains," Arch. Derm., 123: 71-73 (1987).
van Gemert et al., "Temperature Behavior of a Model Port-Wine Stain During Argon Laser Coagulation," Phys. Med. Biol. 27(9): 1089-1104 (1982).
Waldman et al., "Cutaneous Inflammation: Effects of Hydroxy Acids and Eicosanoid Inhibitors on Vascular Permeability," Abstracts 523, 88(4): (1987).
Wang et al., "Characterization of Human Scalp Hairs by Optical Low-Coherence Reflectometry," Optics Letters 20(6): 524-526 (1995).
Warren et al., "Pigmentation Induction by Melanocyte Stimulating Hormone in Human Skin Culture," Abstracts 523, 88(4): (1987).
Wastek et al., "Characterization of H-Substance P (SP) Binding to a Mouse Monoclonal Mast Cell Line (MC/9)," Abstracts 523, 88(4): (1987).
Watanabe et al., "The Effect of Pulse Duration on Selective Pigmented Cell Injury by Dye Lasers," Abstracts 523, 88(4): (1987).
Watanabe et al., "Comparative Studies of Femtosecond to Microsecond Laser Pulses on Selective Pigmented Cell Injury in Skin," Photochemistry and Photobiology 53(6): 757-761 (1991).
Weissman et al., "Growth, Collagen and Glycosaminoglcan Synthesis by Dermal Fibroblasts Derived From Puva Treated and Psoriatic Patients," Abstracts 523, 88(4): (1987).
Welch et al., "Evaluation of Cooling Techniques for the Protection of the Epidermis During Nd: YAG Laser Irradiation of Skin," in Neodymium-YAG Laser in Medicine and Surgery, ed: SN Joffe, Elsevier, New York: 196-204 (1983).
Werse et al., "Effects of Essential Fatty Acid Deficiency on the Structure and Function of Epidermal Lipids," Abstracts 523, 88(4): (1987).
"Workshop on Analysis of Laser-Tissue Interaction for Clinical Treatment," University of Texas, Austin, TX 78712, Jul. 14-18, 1986.
Yules et al., "The Effect of Q-Switched Ruby Laser Radiation on Dermal Tattoo Pigment in Man," Arch. Surg. 95: 179-180 (1967).
Zeitler et al., "Laser Characteristics that Might be Useful in Biology," Laser Applications in Medicine and Biology 1: 1-18 (1971).
International Search Report for PCT/US06/037605 filed on Sep. 28, 2006 (4 pages).

\* cited by examiner

METHOD OF TREATING CELLULITE

CROSS-REFERENCE TO RELATED APPLICATIONS

This application claims priority to and the benefit of U.S. provisional patent application Ser. No. 60/721,272 filed Sep. 28, 2005, the entire disclosure of which is herein incorporated by reference.

FIELD OF THE INVENTION

The invention relates generally to cosmetic treatments, and more particularly to using a beam of radiation to treat subcutaneous fat and strengthen dermal tissue to preclude subcutaneous fat from crossing a dermal interface and entering the dermal region.

BACKGROUND OF THE INVENTION

Cellulite is a common cosmetic problem of skin that appears as an irregularity of skin contour, and is often characterized by a dimpled or bumpy appearance of the skin. Cellulite commonly can be found around the thigh region, buttocks, arms, abdomen, and other regions of the body where large masses of fat can be found in close proximity to the skin surface.

Cellulite can result from fat permeating a dermal interface between a dermal layer and a subcutaneous fat layer of skin, which can be described as herniation of fat into the dermis. Typically, the dermis is weakened, as a result of stretching of the dermal tissue, tissue injury, or hormonal changes. A cellulite bump can result from subcutaneous fat that protrudes and/or permeates into the weakened dermis. A thinning of the dermal layer also can be associated with cellulite.

Cellulite can be treated by an invasive surgical procedure such as liposuction, but an invasive procedure can involve pain, can result in swelling and inflammation of tissue, and can require considerable recovery time. Massage can enhance circulation and lymphatic drainage, resulting in fluids being drained from the area, but massage only provides a temporary improvement in the condition. Repeated massage treatments can be required to maintain a cellulite-free appearance, and massage does not preclude new fat being formed from permeating into the dermal layer.

Treatments that include a massage component and irradiation of the tissue with light or ultrasonic energy have also been proposed to treat cellulite. These systems purport to break down the fat and promote its removal from the tissue, but they can not result in long-lasting benefits, since the normal fat regeneration process can result in the reappearance of cellulite as fatty tissue permeates into the dermal layer.

SUMMARY OF THE INVENTION

The technology, in various embodiments, features an apparatus for treating and a treatment for subcutaneous fat, such as cellulite. The treatment is not limited to cellulite and can be used for any fatty deposit located in or proximate to the dermal interface. Instead of being an invasive surgical procedure, treatment radiation is directed through the surface of the skin. Longer lasting benefits than prior art treatments can be achieved because, in one embodiment, a treatment, injures the fatty tissue and causes a thickening and/or strengthening of the dermis, which can prevent and/or preclude additional fatty tissue from permeating the dermal interface and/or from perturbing the dermal interface. In various embodiments, a treatment can, for example, reduce fat, remove a portion of fat, improve skin laxity, tighten skin, strengthen skin, thicken skin, induce new collagen formation, promote fibrosis of the dermal layer or subcutaneous fat layer, or be used for a combination of the aforementioned. Furthermore, a treatment can include a series of treatment cycles, so that fatty tissue can be reduced gradually, and/or the skin can be tightened gradually, resulting in a more cosmetically appealing appearance.

A treatment can include cooling to protect the skin surface, to minimize unwanted injury to the surface of the skin, and to minimize any pain that a patient may feel. An additional advantage of such a treatment is that the treatment can be performed with minimal acute cosmetic disturbance such that the patient can return to normal activity immediately after the treatment.

In one aspect, the technology features a method of treating a fatty deposit (e.g., cellulite) in a target region of skin. The method includes cooling an epidermal region of the target region of skin, and delivering a beam of radiation to a subcutaneous fat region disposed relative to a dermal interface in the target region of skin (a) to affect at least one fat cell in the subcutaneous fat region without causing substantial unwanted injury to the epidermal region, and (b) to cause thermal injury to a dermal region sufficient to induce collagen formation to strengthen and/or thicken the target region of skin. In various embodiments, the method can be used to strengthen and/or tighten the target region of skin to prevent subcutaneous fat from crossing the dermal interface into the dermal region and/or from perturbing the dermal interface. This can improve the appearance of a region of the body. In one embodiment, the treatment radiation is delivered to the target region in the absence of cooling.

In another aspect, the invention features an apparatus for treating cellulite in a target region of skin. The apparatus includes a source generating a beam of radiation, a delivery system coupled to the source, and a cooling system. The source includes a fiber coupled laser diode array. The delivery system directs the beam of radiation to a subcutaneous fat region disposed relative to a dermal interface in the target region of skin to affect at least one fat cell in the subcutaneous fat region and to cause thermal injury to a dermal region to induce collagen formation to strengthen the target region of skin. The cooling system cools an epidermal region of the target region to minimize substantial unwanted injury thereto.

In still another aspect, the invention features an apparatus for treating cellulite in a target region of skin. The apparatus includes means for cooling an epidermal region of the target region of skin and means for delivering a beam of radiation to a subcutaneous fat region disposed relative to a dermal interface in the target region of skin. The beam of radiation to affect at least one fat cell in the subcutaneous fat region without causing substantial unwanted injury to the epidermal region and to cause thermal injury to a dermal region to induce collagen formation to strengthen the target region of skin.

In yet another aspect, the invention features an apparatus including a source generating a beam of radiation and a housing enclosing the source. The housing includes an aperture to transmit the beam of radiation to a subcutaneous fat region disposed relative to a dermal interface in a target region of skin (a) to affect at least one fat cell in the subcutaneous fat region without causing substantial unwanted injury to the epidermal region, and (b) to cause thermal injury to a dermal region to induce collagen formation to strengthen the target region of skin. The source can include a fiber coupled laser diode array. The apparatus can include a cooling system for cooling an epidermal region of the target region to minimize substantial unwanted injury thereto.

In another aspect, the invention features a kit for improving the cosmetic appearance of a subcutaneous fat region disposed relative to a dermal interface in a target region of skin. The kit includes a source generating a beam of radiation and instruction means including instructions for directing the beam of radiation to the subcutaneous fat region. The beam of radiation affects at least one fat cell in the subcutaneous fat region without causing substantial unwanted injury to the epidermal region and causes thermal injury to a dermal region to induce collagen formation to strengthen the target region of skin. The source can include a fiber coupled laser diode array. The instruction means can control a cooling system for cooling an epidermal region of the target region to minimize substantial unwanted injury thereto. In certain embodiments, the instruction means can prescribe a wavelength, fluence, and pulse duration for treatment of the subcutaneous fat region.

In other examples, any of the aspects above, or any apparatus or method described herein, can include one or more of the following features. In various embodiments, the target region of skin can be strengthened to prevent subcutaneous fat from crossing the dermal interface into the dermal region. In certain embodiments, a fat cell can be damaged so that lipid contained within can escape and at least a portion of the lipid can be carried away from the target region. In some embodiments, a fat cell can be destroyed.

The beam of radiation can be delivered to the target region to thermally injure the at least one fat cell. In certain embodiments, collagen fibers in the dermal region can be partially denatured to strengthen and tighten the target region of skin. Sufficient thermal injury can cause an increase in extracellular matrix constituents for dermal skin rejuvenation. Fibroblasts can be activated to deposit increased amounts of collagen and extracellular matrix constituents in the target region. Thermal injury can induce fibrosis in at least one of the dermal layer, a subcutaneous fat region, at the dermal interface, and proximate to the dermal interface. In some embodiments, the beam of radiation can cause the temperature to peak at the dermal interface.

In various embodiments, the beam of radiation can have a wavelength between about 1,160 nm and 1,800 nm. In certain embodiments, the wavelength can be between about 1,190 nm and about 1,230 nm. In certain embodiments, the wavelength can be between about 1,700 nm and about 1,760 nm. The fluence can be between about 1 J/cm$^2$ and about 500 J/cm$^2$. In some embodiments, the fluence can be between about 10 J/cm$^2$ and about 150 J/cm$^2$. The pulse duration can be between about 0.1 second to 20 seconds. In certain embodiments, the beam of radiation can be delivered as a series of sub-pulses delivered over a time interval of between about 0.1 second to 20 seconds.

In various embodiments, the beam of radiation can be delivered to the target region about 0.5 mm to about 10 mm below the surface of the skin. In some embodiments, the beam of radiation can be delivered to the target region about 1 mm to about 10 mm below the surface of the skin. The target region of the skin can be between about 1 mm and about 5 mm below the surface of the skin.

In various embodiments, the target region of skin can be massaged before, during, or after irradiation of the target region of skin. Massaging can facilitate removal of the treated fatty tissue from the target region. In certain embodiments, the epidermal region of skin can be cooled at least one of before, during, and after delivering the beam of radiation to the interface of the dermal region and the subcutaneous fat region in the target region of skin. An osmotic agent can be applied to the target region of skin to reduce water content in the target region. A module can be used to apply the osmotic agent.

In certain embodiments, a focusing system can be used to focus the beam of radiation below the surface of the skin in the target region to affect the at least one fat cell. The focusing system can include a planoconvex lens and/or a plurality of lens to focus the beam of radiation. A vacuum system can draw the target region of skin against a concave contact surface of a lens to focus the beam of radiation to the at least one fat cell in the target region. The focusing system can direct the beam of radiation to the target region about 0.5 mm to about 5 mm below the exposed surface of the skin. In some embodiments, the fiber coupled laser diode array includes a high power semiconductor laser.

Other aspects and advantages of the invention will become apparent from the following drawings and description, all of which illustrate the principles of the invention, by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DESCRIPTION OF THE INVENTION

Subcutaneous fat and/or cellulite can be treated by injuring fatty tissue (e.g., a fatty deposit located at or proximate to the dermal interface) and by thickening and/or strengthening of the dermis, which can prevent and/or preclude additional fatty tissue from perturbing the dermal interface. In various embodiments, a treatment can, for example, reduce fat, remove a portion of fat, improve skin laxity, tighten skin, strengthen skin, thicken skin, induce new collagen formation, promote fibrosis of the dermal layer or subcutaneous fat layer, or be used for a combination of the aforementioned.

Figure 1:
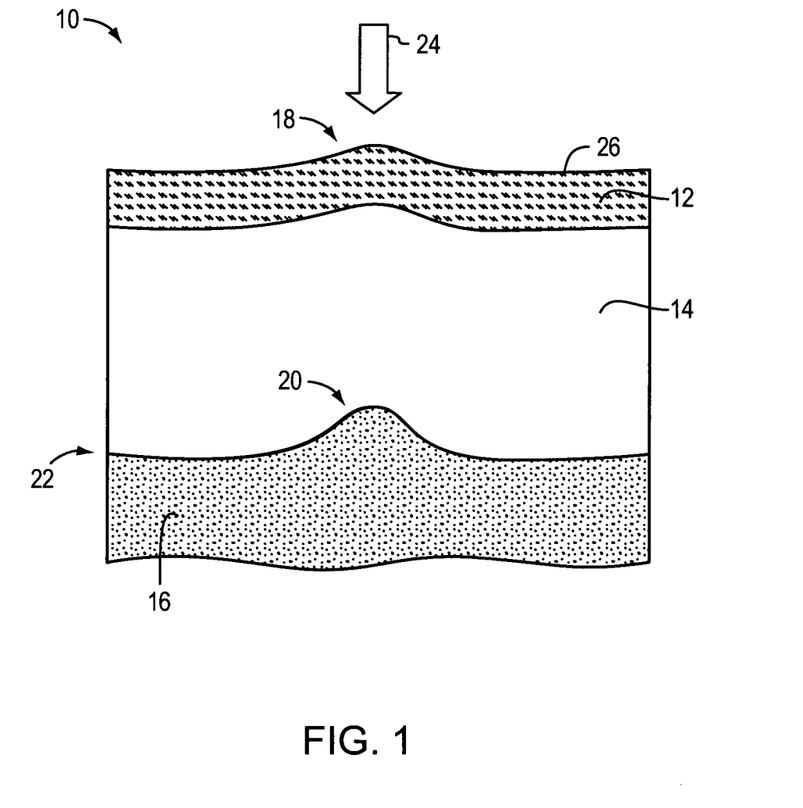
FIG. 1 shows a sectional view of skin including subcutaneous fat being treated by a beam of radiation.

FIG. 1 shows a cross-section of skin 10 including an epidermal layer 12, a dermal layer 14, and a layer of fatty tissue 16. A cellulite bump 18 is formed by a portion 20 of the fatty tissue 16 perturbing the dermal interface 22. The fatty tissue can push into and/or against the dermal interface 22. In some embodiments, a portion of the fatty tissue can permeate or cross the dermal interface 22 and invade the dermal layer 14. A beam of radiation 24 can be used to treat at least a portion of the fatty tissue 16 by delivery through a surface 26 of the epidermal layer 12. The radiation 24 penetrates through the epidermal layer 12 and the dermal layer 14 to treat at least a portion of the dermal layer 14.

The treatment radiation can damage one or more fat cells so that at least a portion of lipid contained within can escape or be drained from the treated region. At least a portion of the lipid can be carried away from the tissue through biological processes. In one embodiment, the body's lymphatic system can drain the treated fatty tissue from the treated region. In an embodiment where a fat cell is damaged, the fat cell can be viable after treatment. In one embodiment, the treatment radiation can destroy one or more fat cells. In one embodiment, a first portion of the fat cells is damaged and a second portion is destroyed. In one embodiment, a portion of the fat cells can be removed to selectively change the shape of the body region.

In some embodiments, the beam of radiation can be delivered to the target region to thermally injure, damage, and/or destroy one or more fat cells. For example, the beam of radiation can be delivered to a target chromophore in the target region. Suitable target chromophores include, but are not limited to, a fat cell, lipid contained within a fat cell, fatty tissue, a wall of a fat cell, water in a fat cell, and water in tissue surrounding a fat cell. The energy absorbed by the chromophore can be transferred to the fat cell to damage or destroy the fat cell. For example, thermal energy absorbed by dermal tissue can be transferred to the fatty tissue. In one embodiment, the beam of radiation is delivered to water within or in the vicinity of a fat cell in the target region to thermally injure the fat cell.

In various embodiments, treatment radiation can affect one or more fat cells and can cause sufficient thermal injury in the dermal region of the skin to elicit a healing response to cause the skin to remodel itself. This can result in more youthful looking skin and an improvement in the appearance of cellulite. In one embodiment, sufficient thermal injury induces fibrosis of the dermal layer, fibrosis on a subcutaneous fat region, or fibrosis in or proximate to the dermal interface. In one embodiment, the treatment radiation can partially denature collagen fibers in the target region. Partially denaturing collagen in the dermis can induce and/or accelerate collagen synthesis by fibroblasts. For example, causing selective thermal injury to the dermis can activate fibroblasts, which can deposit increased amounts of extracellular matrix constituents (e.g., collagen and glycosaminoglycans) that can, at least partially, rejuvenate the skin. The thermal injury caused by the radiation can be mild and only sufficient to elicit a healing response and cause the fibroblasts to produce new collagen. Excessive denaturation of collagen in the dermis causes prolonged edema, erythema, and potentially scarring. Inducing collagen formation in the target region can change and/or improve the appearance of the skin of the target region, as well as thicken the skin, tighten the skin, improve skin laxity, and/or reduce discoloration of the skin.

In various embodiments, a zone of thermal injury can be formed at or proximate to the dermal interface. Fatty tissue has a specific heat that is lower than that of surrounding tissue (fatty tissue, so as the target region of skin is irradiated, the temperature of the fatty tissue exceeds the temperature of overlying and/or surrounding dermal or epidermal tissue. For example, the fatty tissue has a volumetric specific heat of about 1.8 J/cm$^3$ K, whereas skin has a volumetric specific heat of about 4.3 J/cm$^3$ K. In one embodiment, the peak temperature of the tissue can be caused to form at or proximate to the dermal interface. For example, a predetermined wavelength, fluence, pulse duration, and cooling parameters can be selected to position the peak of the zone of thermal injury at or proximate to the dermal interface. This can result in collagen being formed at the bottom of the dermis and/or fibrosis at or proximate to the dermal interface. As a result, the dermal interface can be strengthened against fat herniation. For example, strengthening the dermis can result in long-term improvement of the appearance of the skin since new fat being formed or untreated fat proximate the dermal interface can be prevented and/or precluded from crossing the dermal interface into the dermis.

In one embodiment, fatty tissue is heated by absorption of radiation, and heat can be conducted into dermal tissue proximate the fatty tissue. The fatty tissue can be disposed in the dermal tissue and/or can be disposed proximate to the dermal interface. A portion of the dermal tissue (e.g., collagen) can be partially denatured or can suffer another form of thermal injury, and the dermal tissue can be thickened and/or be strengthened as a result of the resulting healing process. In such an embodiment, a fat-selective wavelength of radiation can be used.

In one embodiment, water in the dermal tissue is heated by absorption of radiation. The dermal tissue can have disposed therein fatty tissue and/or can be overlying fatty tissue. A portion of the dermal tissue (e.g., collagen) can be partially denatured or can suffer another form of thermal injury, and the dermal tissue can be thickened and/or be strengthened as a result of the resulting healing process. A portion of the heat can be transferred to the fatty tissue, which can be affected. In one embodiment, water in the fatty tissue absorbs radiation directly and the tissue is affected by heat. In such embodiments, a water selective wavelength of radiation can be used.

In various embodiments, a treatment can cause minimal cosmetic disturbance so that a patient can return to normal activity following a treatment. For example, a treatment can be performed without causing discernable side effects such as bruising, open wounds, burning, scarring, or swelling. Furthermore, because side effects are minimal, a patient can return to normal activity immediately after a treatment or within a matter of hours, if so desired.

Figure 2:
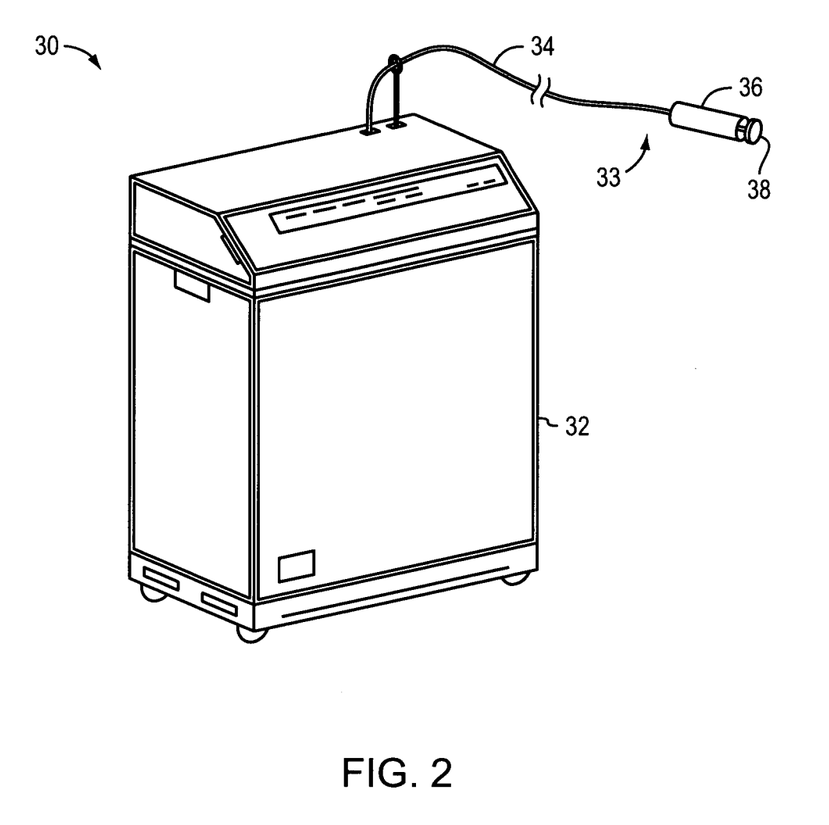
FIG. 2 shows an exemplary system for treating fatty tissue.

FIG. 2 shows an exemplary embodiment of a system 30 for treating tissue. The system 30 can be used to non-invasively deliver a beam of radiation to a target region. For example, the beam of radiation can be delivered through an external surface of skin over the target region. The system 30 includes an energy source 32 and a delivery system 33. In one embodiment, a beam of radiation provided by the energy source 32 is directed via the delivery system 33 to a target region. In the illustrated embodiment, the delivery system 33 includes a fiber 34 having a circular cross-section and a handpiece 36. A beam of radiation can be delivered by the fiber 34 to the handpiece 36, which can include an optical system (e.g., an optic or system of optics) to direct the beam of radiation to the target region. A user can hold or manipulate the handpiece 36 to irradiate the target region. The delivery system 13 can be positioned in contact with a skin surface, can be positioned adjacent a skin surface, can be positioned proximate a skin surface, can be positioned spaced from a skin surface, or a combination of the aforementioned. In the embodiment shown, the delivery system 33 includes a spacer 38 to space the delivery system 33 from the skin surface. In one embodiment, the spacer 38 can be a distance gauge, which can aid a practitioner with placement of the delivery system 33.

In various embodiments, the energy source 32 can be an incoherent light source, a coherent light source (e.g., a laser), a microwave generator, or a radio-frequency generator. In one embodiment, the source generates ultrasonic energy that is used to treat the tissue. In some embodiments, two or more sources can be used together to effect a treatment. For example, an incoherent source can be used to provide a first beam of radiation while a coherent source provides a second beam of radiation. The first and second beams of radiation can share a common wavelength or can have different wavelengths. In an embodiment using an incoherent light source or a coherent light source, the beam of radiation can be a pulsed beam, a scanned beam, or a gated continuous wave (CW) beam. In one embodiment, the source includes an ultrasonic energy device to disrupt or destroy fat cells and a radiation source to induce collagen formation or improve skin laxity.

In various embodiments, the beam of radiation can have a wavelength between about 1000 nm and about 2,600 nm, although longer and shorter wavelengths can be used depending on the application. In some embodiments, the wavelength can be between about 1,000 nm and about 2,200 nm. In other embodiments, the wavelength can be between about 1,160 nm and about 1,800 nm. In yet other embodiments, the wavelength can be between about 1,190 nm and about 1,230 nm or between about 1,700 nm and about 1,760 nm. In one embodiment, the wavelength is about 1,210 nm or about 1,720 nm. In one detailed embodiment, the wavelength is about 1,208 nm, 1,270 nm, 1,310 nm, 1,450 nm, 1,550 nm, 1,720 nm, 1,930 nm, or 2,100 nm. One or more of the wavelengths used can be within a range of wavelengths that can be transmitted to fatty tissue and absorbed by the fatty tissue in the target region of skin.

In various embodiments, the beam of radiation can have a fluence between about 1 J/cm$^2$ and about 500 J/cm$^2$, although higher and lower fluences can be used depending on the application. In some embodiments, the fluence can be between about 10 J/cm$^2$ and about 150 J/cm$^2$. In one embodiment, the fluence is between about 5 J/cm$^2$ and about 100 J/cm$^2$.

In various embodiments, the beam of radiation can have a spotsize between about 0.5 mm and about 25 mm, although larger and smaller spotsizes can be used depending on the application.

In various embodiments, the beam of radiation can have a pulse duration between about 10 µs and about 30 s, although larger and smaller pulse durations can be used depending on the application. In one embodiment, the beam of radiation can have a pulse duration between about 0.1 second and about 20 seconds. In one embodiment, the beam of radiation can have a pulse duration between about 1 second and 20 seconds. In certain embodiments, the beam of radiation can be delivered in a series of sub-pulses spaced in time such that within a region of tissue, the tissue is exposed to radiation intermittently over total time interval of between about 0.1 second and about 20 seconds.

In various embodiments, the beam of radiation can be delivered at a rate of between about 0.1 pulse per second and about 10 pulses per second, although faster and slower pulse rates can be used depending on the application.

In various embodiments, the parameters of the radiation can be selected to deliver the beam of radiation to a predetermined depth. In some embodiments, the beam of radiation can be delivered to the target region about 0.5 mm to about 10 mm below an exposed surface of the skin, although shallower or deeper depths can be selected depending on the application. In one embodiment, the beam of radiation is delivered to the target region about 1 mm to about 10 mm below an exposed surface of the skin.

In various embodiments, the tissue can be heated to a temperature of between about 50° C. and about 80° C., although higher and lower temperatures can be used depending on the application. In one embodiment, the temperature is between about 55° C. and about 70° C.

To minimize unwanted thermal injury to tissue not targeted (e.g., an exposed surface of the target region and/or the epidermal layer), the delivery system 33 shown in FIG. 2 can include a cooling system for cooling before, during or after delivery of radiation, or a combination of the aforementioned. Cooling can include contact conduction cooling, evaporative spray cooling, convective air flow cooling, or a combination of the aforementioned. In one embodiment, the handpiece 36 includes a skin contacting portion that can be brought into contact with the skin. The skin contacting portion can include a sapphire or glass window and a fluid passage containing a cooling fluid. The cooling fluid can be a fluorocarbon type cooling fluid, which can be transparent to the radiation used. The cooling fluid can circulate through the fluid passage and past the window to cool the skin.

A spray cooling device can use cryogen, water, or air as a coolant. In one embodiment, a dynamic cooling device can be used to cool the skin (e.g., a DCD available from Candela Corporation). For example, the delivery system 33 shown in FIG. 2 can include tubing for delivering a cooling fluid to the handpiece 36. The tubing can be connected to a container of a low boiling point fluid, and the handpiece can include a valve for delivering a spurt of the fluid to the skin. Heat can be extracted from the skin by virtue of evaporative cooling of the low boiling point fluid. The fluid can be a non-toxic substance with high vapor pressure at normal body temperature, such as a Freon, tetrafluoroethane, or liquefied $CO_2$.

The time duration of cooling and of radiation application can be adjusted to maximize heating and thermal injury to the region proximate to the dermal interface. In tissue where the dermal interface is deeply situated, the cooling time can be lengthened such that cooling can be extended deeper into the skin. At the same time, the time duration of radiation application can be lengthened such that heat generated by the radiation in the region of dermis closer to the skin surface can be removed via thermal conduction and blood flow, thereby minimizing injury to the tissue overlying the dermal interface. Similarly if the dermis overlying the dermal interface is thin, the time duration of cooling and of radiation application can be adjusted to be shorter, such that thermal injury is confined to the region proximate to the dermal interface.

In various embodiments, a topical osmotic agent is applied to the region of skin to be treated, prior to treatment. The osmotic agent reduces the water content in the dermis overlying the dermal interface. This reduction in the water content can increase the transmission of the radiation into the dermal interface region and into the subcutaneous fat, thereby more effectively treating the area, reducing injury to the dermis, and reducing treatment pain. The osmotic agent can be glycerin or glycerol. A module can be used to apply the osmotic agent. The module can be a needle or syringe. The module can include a reservoir for retaining the osmotic agent and an injector for applying the agent to a skin region.

In various embodiments, a delivery system can include a focusing system for focusing the beam of radiation below the surface of the skin in the target region to affect at least one fat cell. The focusing system can direct the beam of radiation to the target region about 0.1 mm to about 10 mm below the exposed surface of the skin. In some embodiments, the delivery system can include a lens, a planoconvex lens, or a plurality of lens to focus the beam of radiation.

Figure 3:
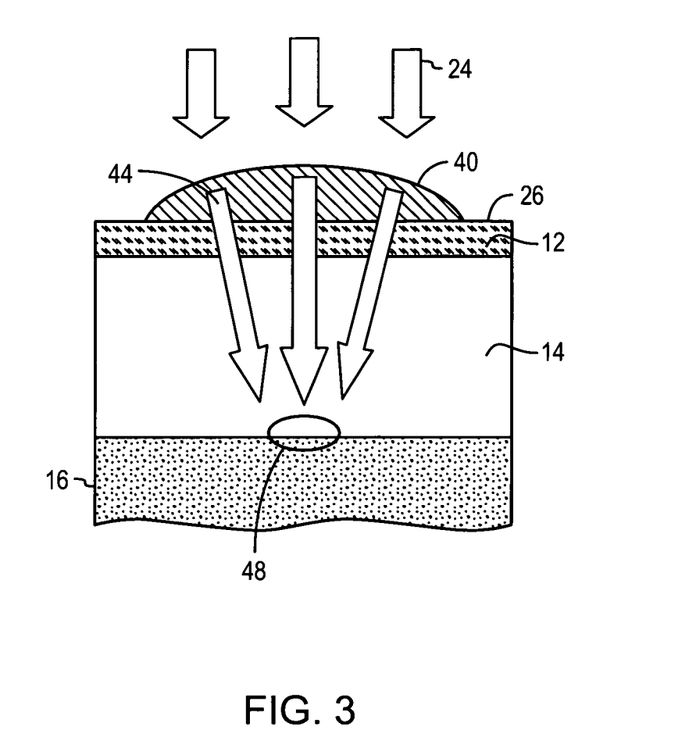
FIG. 3 depicts a planoconvex lens positioned on a skin surface.

FIG. 3 shows a planoconvex lens 40 positioned on a surface 26 of a section of skin, including an epidermal region 12, a dermal region 14, and a layer of fatty tissue 16. The planoconvex lens 40 focuses radiation 24 (focusing shown by arrows 44) to a sub surface focal region 48, which can include at least one fat cell. In certain embodiments, the element contacting the skin can be pressed into or against the skin to displace blood in the dermis, thereby increasing the transmission of the radiation through the dermis and reducing unwanted injury to the skin.

Figure 4:
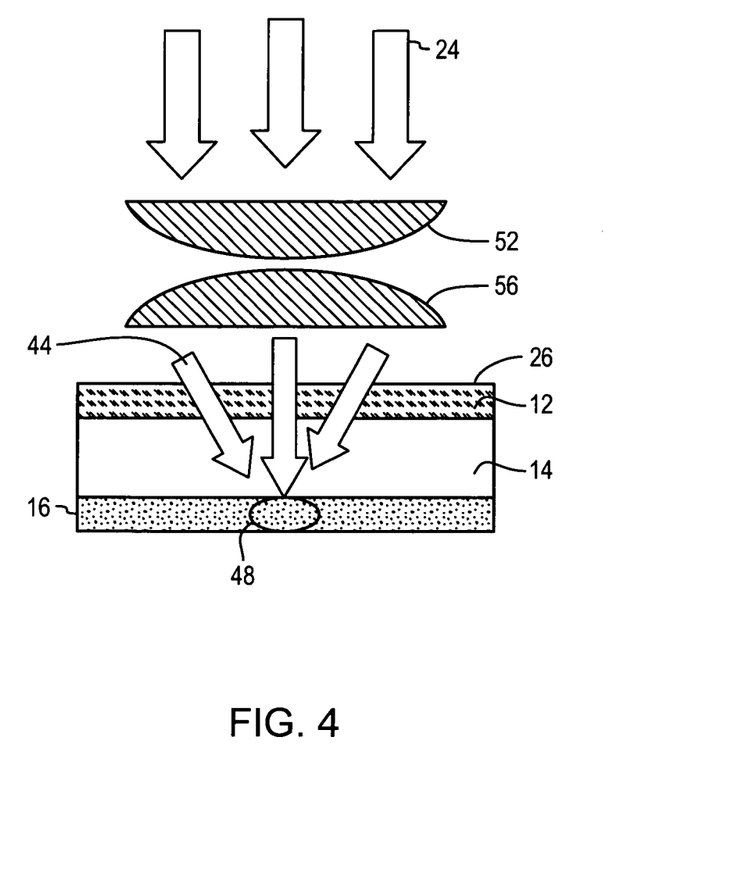
FIG. 4 shows a plurality of lens focusing radiation to a target region of skin.

FIG. 4 shows a plurality of lens 52, 56 spaced from the skin surface 26. The plurality of lens 52, 56 focus the radiation 24 (focusing shown by the arrows 44) to the sub surface focal region 48.

Figure 5:
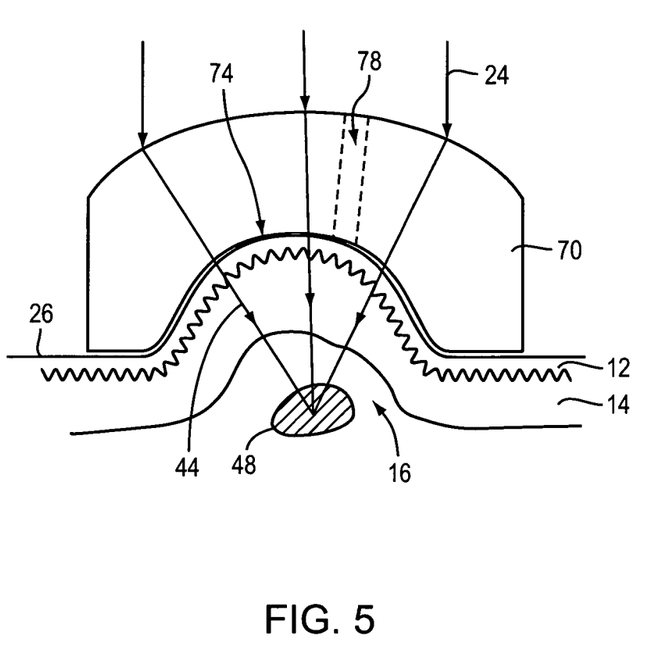
FIG. 5 shows a lens having a concave surface positioned on a skin surface.

FIG. 5 shows a lens 70 having a concave surface 74 for contacting the skin surface 26. In certain embodiments, the lens 70 is placed proximate to a target region of skin. Vacuum can be applied to draw the target region of skin against the concave surface 74 of the lens 70. Vacuum can be applied through orifice 78 in the lens 70 by a vacuum device. The lens 70 focuses the radiation 24 to the sub surface focal region 48.

In various embodiments, the source of radiation can be a diode laser having sufficient power to affect one or more fat cells. An advantage of diode lasers is that they can be fabricated at specific wavelengths that target fatty tissue. A limitation, though, of many diode laser devices and solid state devices targeting fatty tissue is the inability to produce sufficient power to effectuate a successful treatment.

In one embodiment, a diode laser of the invention is a high powered semiconductor laser. In one embodiment, the source of radiation is a fiber coupled diode laser array. For example, an optical source of radiation can include a plurality of light sources (e.g., semiconductor laser diodes) each adapted to emit a beam of light from a surface thereof. A plurality of first optical fibers each can have one end thereof adjacent the light emitting surface of a separate one of the light sources so as to receive the beam of light emitted therefrom. The other ends of the first optical fibers can be bundled together in closely spaced relation so as to effectively emit a single beam of light, which is a combination of the beams from all of the first optical fibers. A second optical fiber can have an end adjacent the other ends of the first optical fibers to receive the beam of light emitted from the bundle of first optical fibers. The beam of light from the bundled other ends of the first optical fibers can be directed into the second optical fiber. The first optical fiber can have a numerical aperture less than that of the second fiber. An exemplary fiber coupled diode laser array is described in U.S. Pat. No. 5,394,492, owned by the assignee of the instant application and the entire disclosure of which is herein incorporated by reference.

In various embodiments, beams from multiple diode lasers or diode laser bars can be combined using one or more lens. In one embodiment, an array of diode lasers is mounted in a handpiece of the delivery system, and respective beams of radiation from each diode laser can be directed to the target region. The beams of radiation can be combined so that they are incident at substantially the same point. In one embodiment, the one or more lens direct the multiple beams of radiation into a single optical fiber. A handpiece of the delivery system projects the combined beam of radiation to the target region of skin.

In various embodiments, a laser diode array can include a plurality of discrete emitter sections mounted on a substrate, e.g., a laser bar. Each discrete emitter section can include a light emitting material having an active region and an inactive region. Each discrete emitter section can be a laser diode. The substrate provides electrical isolation between adjacent discrete emitter sections. A plurality of wire bonds can connect electrically the plurality of discrete emitter sections in a series configuration. Each discrete emitter section can be physically isolated from an adjacent discrete emitter section by, for example, mechanically dicing to remove a portion of the inactive region. In various embodiments, the light emitting material is a semiconductor material. Suitable semiconductor materials include InGaAlP, InGaP, InGaAs, InGaN, or InGaAsP. In one embodiment, the active region is InGaAs, and the inactive region is GaAs. In various embodiments, the substrate can be diamond, ceramic, BeO, alumina, or a gold plated ceramic. The light emitting material can be soldered to the substrate, e.g., using tin-containing solders such as SnBi, SnPb, and SnPbAg (e.g., Sn62) and gold-containing solders such as AuGe. An exemplary laser diode array is described in U.S. patent application Ser. No. 11/503,492 file Aug. 11, 2006, owned by the assignee of the instant application and the entire disclosure of which is herein incorporated by reference.

Figure 6A:
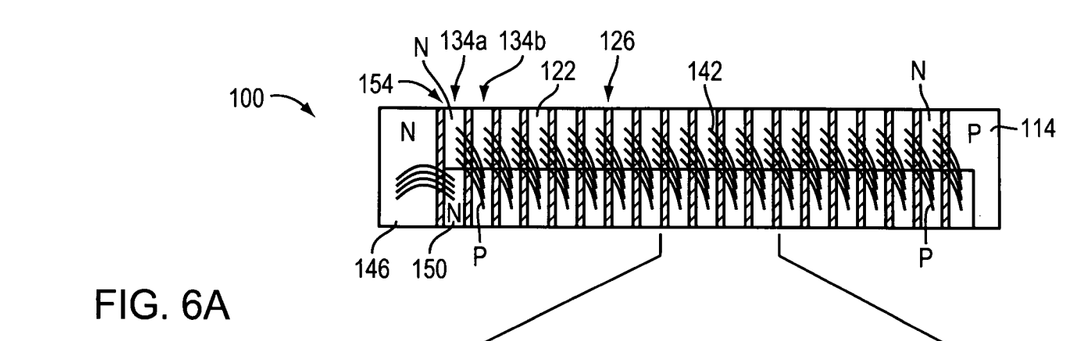
FIG. 6A shows a plan view of a laser diode array.
Figure 6B:
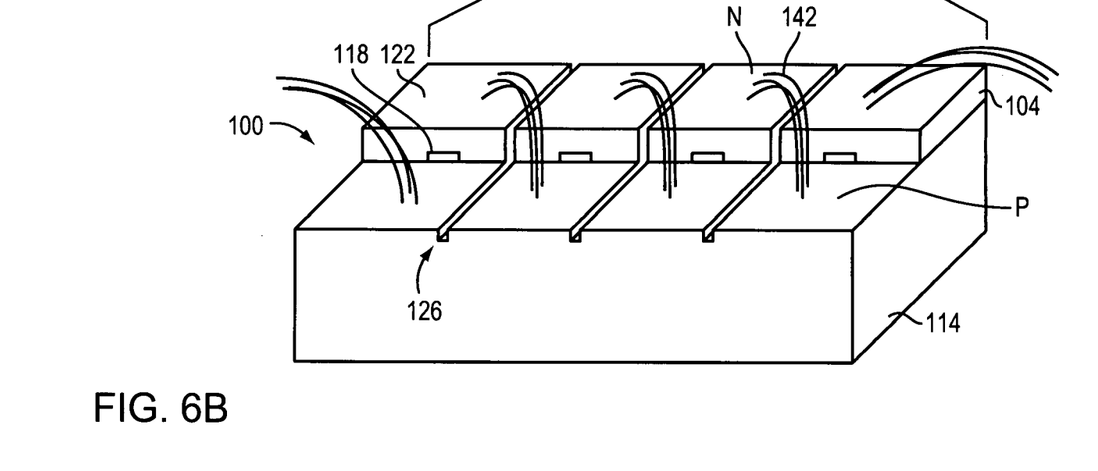
FIG. 6B shows an enlarged perspective view of the laser diode array of FIG. 6A.

FIGS. 6A and 6B shows a laser diode array 100 including a light emitting material 104 formed on a substrate 114. The light emitting material 104 includes one or more active regions 118 and an inactive region 122. Cuts 126 can be positioned between adjacent active regions 118 to form a plurality of discrete emitter sections 134. Cuts 126 can be removal points or dicing points. Each discrete emitter section 134 can be electrically and/or physically isolated from an adjacent discrete emitter section. FIG. 6B shows a first n-type region 146 connected to a second n-type region 150 over an isolation cut 154 so that an operator can have a soldering point for connecting to a drive circuit. The remaining connections are formed between an n-type region and an adjacent p-type region. For example, a n-type region of a first discrete emitter section 134a of the light emitting material 104 can be electrically coupled to a p-type region of a second discrete emitter section 134b. The p-type region can be electrically coupled to a portion of the substrate 114, and the n-type region of the first discrete emitter section 134a can be connected to that substrate 114 portion. For example, FIG. 6B shows an enlarged view of four discrete emitter sections 134 of the laser diode array 100 where the wire 142 is bonded to the substrate 114.

In certain embodiments, a p-type region of a first discrete emitter section 134 of the light emitting material 104 can be electrically coupled to a n-type region of a second discrete emitter section 134. The n-type region can be electrically coupled to a portion of the substrate 114, and the p-type region of the first discrete emitter section 134 can be connected to that substrate 114 portion.

Figure 7:
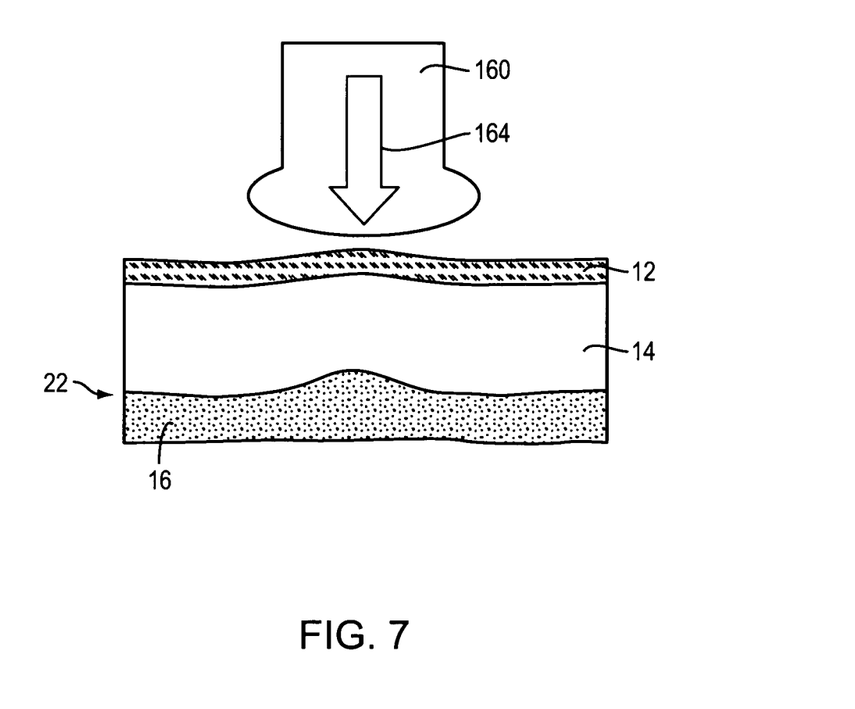
FIG. 7 shows a handpiece of an ultrasound device placed proximate to a skin surface.

In various embodiments, an ultrasound device can be used to measure the depth or position of the fatty tissue. For example, a high frequency ultrasound device can be used. FIG. 7 shows a handpiece of an ultrasound device 160 placed proximate to the skin to make a measurement. In one embodiment, the ultrasound device 160 can be place in contact with the skin surface. The ultrasound device 160 can deliver ultrasonic energy 164 to measure position of the dermal interface 22, so that radiation can be directed to the interface 22, as shown, e.g., in FIGS. 1, 3-5, and 8.

The time duration of the cooling and of the radiation application can be adjusted so as to maximize the thermal injury to the vicinity of the dermal interface 22. For example, if the position of the fatty tissue is known, then parameters of the optical radiation, such as pulse duration and/or fluence, can be optimized for a particular treatment. Cooling parameters, such as cooling time and/or delay between a cooling and irradiation, can also be optimized for a particular treatment. Accordingly, a zone of thermal treatment can be predetermined and/or controlled based on parameters selected. For example, the zone of thermal injury can be positioned in or proximate to the dermal interface.

Figure 8:
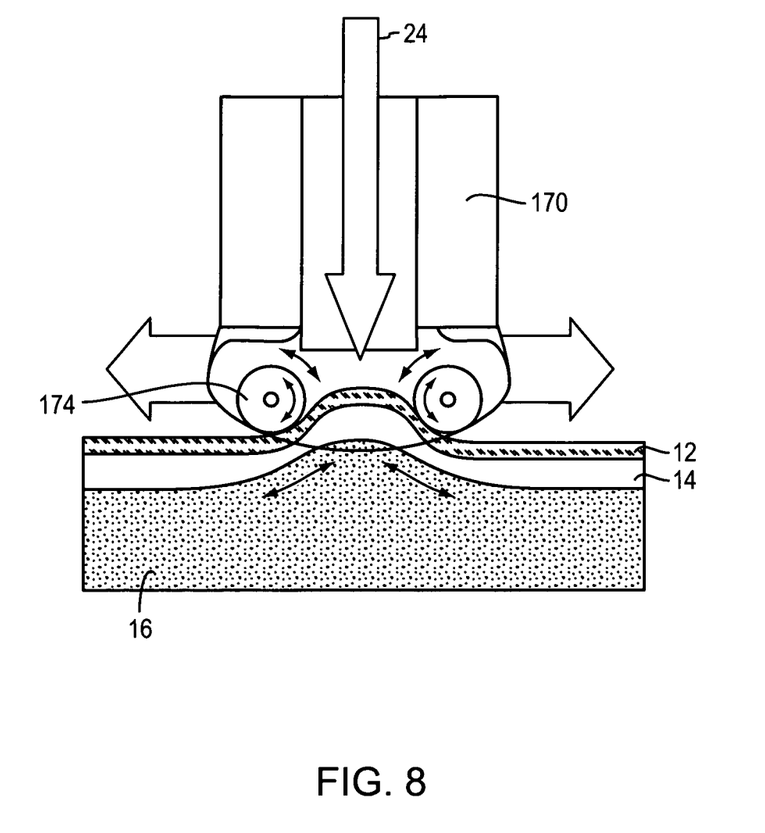
FIG. 8 depicts a handpiece used to massage the skin.

In various embodiments, the target region of skin can be massaged before, during, and/or after irradiation of the target region of skin. The massage can be a mechanical massage or can be manual massage. FIG. 8 depicts a handpiece 170 that includes rollers 174 to massage the skin. Radiation 24 can be delivered through a central portion of the handpiece 170. The massage handpiece 170 can be adapted to fit over the delivery system 13 shown in FIG. 2. In one embodiment, a delivery system can be formed with a mechanical massage device affixed. In one embodiment, vacuum can be used to pull the tissue into the device, which can provide an additional massage effect. In one embodiment, a person massages the target region of skin after irradiation of the tissue. Massaging the target region of skin can facilitate removal of the treated fatty tissue from the target region. For example, massaging can facilitate draining of the treated fatty tissue from the treated region.

The invention features a kit suitable for use in the treatment of subcutaneous fat and/or cellulite. The kit can be used to improve the cosmetic appearance of a region of skin. The kit can include a source of a beam of radiation and instruction means. The instruction means can include instructions for directing the beam of radiation to a subcutaneous fat region. The beam of radiation can affect at least one fat cell in the subcutaneous fat region without causing substantial unwanted injury to the epidermal region and cause thermal injury to a dermal region to induce collagen formation to strengthen the target region of skin. The source can include a fiber coupled laser diode array. A cooling system can be used to cool an epidermal region of the target region to minimize substantial unwanted injury thereto. The instruction means can prescribe a wavelength, fluence, and/or pulse duration for treatment of the subcutaneous fat region. The instruction means, e.g., treatment guidelines, can be provided in paper form, for example, as a leaflet, booklet, book, manual, or other like, or in electronic form, e.g., as a file recorded on a computer readable medium such as a drive, CD-ROM, DVD, or the like.

In some embodiments, the instruction means can be implemented in digital electronic circuitry, or in computer hardware, firmware, software, or in combinations of them. The implementation can be as a computer program product, i.e., a computer program tangibly embodied in an information carrier, e.g., in a machine-readable storage device or in a propagated signal, for execution by, or to control the operation of, data processing apparatus, e.g., a programmable processor, a computer, or multiple computers. A computer program can be written in any form of programming language, including compiled or interpreted languages, and the computer program can be deployed in any form, including as a stand-alone program or as a subroutine, element, or other unit suitable for use in a computing environment. A computer program can be deployed to be executed on one computer or on multiple computers at one site.

The instruction means can be performed by one or more programmable processors executing a computer program to perform functions of the technology by operating on input data and generating output. The instruction means can also be performed by, and an apparatus can be implemented as, special purpose logic circuitry, e.g., an FPGA (field programmable gate array) or an ASIC (application-specific integrated circuit). Subroutines can refer to portions of the computer program and/or the processor/special circuitry that implements that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer also includes, or be operatively coupled to receive data from or transfer data to, or both, one or more mass storage devices for storing data, e.g., magnetic, magneto-optical disks, or optical disks. Data transmission and instructions can also occur over a communications network. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

To provide for interaction with a user, the above described techniques can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer (e.g., interact with a user interface element). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The above described techniques can be implemented in a distributed computing system that includes a back-end component, e.g., as a data server, and/or a middleware component, e.g., an application server, and/or a front-end component, e.g., a client computer having a graphical user interface and/or a Web browser through which a user can interact with an example implementation, or any combination of such back-end, middleware, or front-end components. The components of the system can be interconnected by any form or medium of digital data communication, e.g., a communication network. Examples of communication networks include a local area network ("LAN") and a wide area network ("WAN"), e.g., the Internet, and include both wired and wireless networks.

The computing system can include clients and servers. A client and a server are generally remote from each other and typically interact through a communication network. The relationship of client and server arises by virtue of computer programs running on the respective computers and having a client-server relationship to each other.

While the technology has been particularly shown and described with reference to specific illustrative embodiments, it should be understood that various changes in form and detail may be made without departing from the spirit and scope of the technology.

What is claimed:

1. A method of treating cellulite in a target region of skin, comprising:
    cooling an epidermal region overlying the target region of skin;
    delivering radiation to a dermal interface in the target region of skin, the radiation having a wavelength between about 1,190 nm and about 1,230 nm;
    heating the dermal interface in the target region of skin to a temperature above 60° Celsius and below 80° Celsius to remove at least one fat cell in the target region of skin without causing substantial unwanted injury to the epidermal region and to cause thermal injury to the dermal interface to induce collagen formation to cause fibrosis in the target region of skin; and generating the radiation having a pulse duration of about 3 seconds to about 30 seconds.

2. The method of claim 1 further comprising delivering the radiation to the target region about 0.5 mm to about 10 mm below the surface of the skin.

3. The method of claim 1 further comprising cooling the epidermal region of skin at least one of before, during, and after delivering the radiation to the interface of the dermal region and the subcutaneous fat region in the target region of skin.

4. The method of claim 1 further comprising massaging the target region of skin before, during, or after irradiation of the target region of skin.

5. The method of claim 1 further comprising applying an osmotic agent to the target region of skin to reduce water content in the target region.

6. The method of claim 1 further comprising delivering the radiation to cause the temperature to peak at the dermal interface.

7. A method of treating cellulite in a target region of skin, comprising:
   cooling an epidermal region overlying the target region of skin;
   delivering radiation to a dermal interface in the target region of skin, the radiation having a wavelength between about 1,190 nm and about 1,230 nm;
   heating the dermal interface in the target region of skin to a temperature above 60° Celsius and below 80° Celsius to remove at least one fat cell in the target region of skin without causing substantial unwanted injury to the epidermal region and to cause thermal injury to the dermal interface to induce collagen formation to cause fibrosis in the target region of skin; and
   generating the radiation having a pulse duration from about 3 seconds to about 10 seconds.

8. The method of claim 7 further comprising delivering the radiation to the target region about 0.5 mm to about 10 mm below the surface of the skin.

9. The method of claim 7 further comprising cooling the epidermal region of skin at least one of before, during, and after delivering the radiation to the interface of the dermal region and the subcutaneous fat region in the target region of skin.

10. The method of claim 7 further comprising massaging the target region of skin before, during, or after irradiation of the target region of skin.

11. The method of claim 7 further comprising applying an osmotic agent to the target region of skin to reduce water content in the target region.

12. The method of claim 7 further comprising delivering the radiation to cause the temperature to peak at the dermal interface.

13. A method of treating cellulite in a target region of skin, comprising:
   cooling an epidermal region overlying the target region of skin;
   delivering radiation to a dermal interface in the target region of skin, the radiation having a wavelength between about 1,190 nm and about 1,230 nm;
   heating the dermal interface in the target region of skin to a temperature above 60° Celsius and below 80° Celsius to remove at least one fat cell in the target region of skin without causing substantial unwanted injury to the epidermal region and to cause thermal injury to the dermal interface to induce collagen formation to cause fibrosis in the target region of skin; and
   generating the radiation having a fluence of about 80 J/cm to about 170 J/cm.

14. The method of claim 13 further comprising delivering the radiation to the target region about 0.5 mm to about 10 mm below the surface of the skin.

15. The method of claim 13 further comprising cooling the epidermal region of skin at least one of before, during, and after delivering the radiation to the interface of the dermal region and the subcutaneous fat region in the target region of skin.

16. The method of claim 13 further comprising massaging the target region of skin before, during, or after irradiation of the target region of skin.

17. The method of claim 13 further comprising applying an osmotic agent to the target region of skin to reduce water content in the target region.

18. The method of claim 13 further comprising delivering the radiation to cause the temperature to peak at the dermal interface.

* * * * *